US009278079B2

(12) United States Patent
Adkins, Jr. et al.

(10) Patent No.: US 9,278,079 B2
(45) Date of Patent: Mar. 8, 2016

(54) OCULAR COMPOSITION AND KITS THEREOF

(71) Applicant: OCuSOFT, Inc., Richmond, TX (US)

(72) Inventors: Nat Adkins, Jr., Richmond, TX (US); Cynthia Barratt, Richmond, TX (US)

(73) Assignee: OCuSOFT, Inc., Richmond, TX (US)

( * ) Notice: Subject to any disclaimer, the term of this patent is extended or adjusted under 35 U.S.C. 154(b) by 0 days.

(21) Appl. No.: 13/941,010

(22) Filed: Jul. 12, 2013

(65) Prior Publication Data

US 2015/0017213 A1    Jan. 15, 2015

(51) Int. Cl.

| A61F 9/00 | (2006.01) |
|---|---|
| A61K 31/155 | (2006.01) |
| A61K 8/34 | (2006.01) |
| A61K 31/047 | (2006.01) |
| A61K 9/00 | (2006.01) |
| A61K 47/02 | (2006.01) |
| A61K 47/10 | (2006.01) |
| A61K 47/14 | (2006.01) |
| A61K 47/26 | (2006.01) |
| A61K 47/34 | (2006.01) |

(52) U.S. Cl.
CPC .............. *A61K 31/155* (2013.01); *A61K 9/0014* (2013.01); *A61K 31/047* (2013.01); *A61K 47/02* (2013.01); *A61K 47/10* (2013.01); *A61K 47/14* (2013.01); *A61K 47/26* (2013.01); *A61K 47/34* (2013.01); *A61F 9/0008* (2013.01)

(58) Field of Classification Search
None
See application file for complete search history.

(56) References Cited

U.S. PATENT DOCUMENTS

| 2,573,791 A | 4/1947 | Howells |
| 3,068,863 A | 12/1962 | Bowman |
| 3,092,103 A | 6/1963 | Mower |
| 1,167,249 A | 10/1969 | Ambler et al. |
| 3,908,645 A | 9/1975 | Sandvig |
| 4,654,208 A | 3/1987 | Stockel et al. |
| 4,682,371 A | 7/1987 | Heltman |
| 4,758,595 A | 7/1988 | Ogunbiyi et al. |
| 4,904,698 A | 2/1990 | Adkins, Jr. et al. |
| 5,246,695 A | 9/1993 | Hintz et al. |
| 5,431,622 A | 7/1995 | Pyrozyk et al. |
| 5,470,875 A | 11/1995 | Merianos et al. |
| 5,662,624 A | 9/1997 | Sundstrom et al. |
| 5,702,992 A | 12/1997 | Martin et al. |
| 5,769,806 A | 6/1998 | Radow |
| 5,879,378 A | 3/1999 | Usui |
| 5,942,218 A | 8/1999 | Kirschner et al. |
| 6,045,817 A | 4/2000 | Ananthapadmanabhan et al. |
| 6,090,060 A | 7/2000 | Radow |
| 6,112,900 A | 9/2000 | Adkins, Jr. |
| 6,207,628 B1 | 3/2001 | Soyer et al. |
| 6,257,759 B1 | 7/2001 | Wintosky et al. |
| 6,320,094 B1 | 11/2001 | Arnold et al. |
| 6,409,746 B1 | 6/2002 | Igaki et al. |
| 6,604,854 B1 | 8/2003 | Limburg et al. |
| 6,623,517 B1 | 9/2003 | De Luisa et al. |
| 6,629,964 B1 | 10/2003 | Ono et al. |
| 6,642,198 B2 | 11/2003 | Pflederer et al. |
| 6,846,846 B2 | 1/2005 | Modek et al. |
| 7,231,922 B2 | 6/2007 | Davison et al. |
| 7,951,387 B2 | 5/2011 | Witham et al. |
| 8,202,853 B2* | 6/2012 | Adkins, Jr. ............... A61K 8/20 514/152 |
| 8,281,445 B2 | 10/2012 | Adkins, Jr. et al. |
| 2001/0036964 A1 | 11/2001 | Clarkson et al. |
| 2002/0128170 A1 | 9/2002 | DeClercq et al. |
| 2004/0259951 A1 | 12/2004 | Clarkson et al. |
| 2005/0022823 A1 | 2/2005 | Davison et al. |
| 2005/0048139 A1 | 3/2005 | Modak et al. |
| 2005/0238602 A1 | 10/2005 | Modek et al. |
| 2005/0261401 A1 | 11/2005 | Wood et al. |
| 2005/0281762 A1 | 12/2005 | Modek et al. |
| 2006/0036220 A1 | 2/2006 | Kawahara et al. |
| 2006/0045858 A1 | 3/2006 | Fuller |
| 2006/0093634 A1 | 5/2006 | Lutz et al. |
| 2006/0210616 A1 | 9/2006 | Linder |
| 2006/0246013 A1 | 11/2006 | Adkins, Jr. et al. |
| 2007/0110792 A9 | 5/2007 | Simon |
| 2009/0137533 A1 | 5/2009 | Adkins, Jr. |

(Continued)

FOREIGN PATENT DOCUMENTS

| WO | 02092049 A2 | 11/2002 |
| WO | 0292049 A3 | 4/2003 |

(Continued)

OTHER PUBLICATIONS

The Dry Eye Shop 2011 Catalog.*
Assignment of U.S. Appl. No. 13/941,010 to Ocusoft, Inc. (Reel/Frame 030970/0112).*
Walgreens.com webpage for Ocusoft Lid Scrub Original Formula Eyelid Cleanser Pre-Moistened Pads (accessed Dec. 5, 2014).*

(Continued)

*Primary Examiner* — Bethany Barham
*Assistant Examiner* — Peter Anthopolos
(74) *Attorney, Agent, or Firm* — D'Ambrosio & Menon, PLLC; Usha Menon

(57) ABSTRACT

An ocular composition consisting essentially of purified water, PEG-80 sorbitan laurate, sodium trideceth sulfate, PEG-150 distearate, sodium lauroamphoacetate, cocamidopropyl hydroxysultaine, sodium laureth-13 carboxylate, sodium chloride, PEG-15 cocopolyamine, polyhexamethylene biguanide, potassium sorbate, 1,2 hexanediol, and caprylyl glycol. The composition can be applied to a fabric pad for use as an eyelid cleanser, where the fabric pad is pre-moistened with the composition and packaged for use. The composition may also be used in an eyelid treatment kit for convenient combination treatments to improve overall eyelid hygiene and adjunctive eyelid therapy.

19 Claims, No Drawings

(56) References Cited

U.S. PATENT DOCUMENTS

| | | |
|---|---|---|
| 2009/0312337 A1 | 12/2009 | Graham et al. |
| 2010/0239518 A1 | 9/2010 | Matsumura et al. |

FOREIGN PATENT DOCUMENTS

| | | |
|---|---|---|
| WO | 03069994 A1 | 8/2003 |
| WO | 2004064817 A1 | 8/2004 |
| WO | 2005097130 A1 | 10/2005 |
| WO | 2006045743 A1 | 5/2006 |
| WO | 2007120817 A2 | 10/2007 |

OTHER PUBLICATIONS

Arch Personal Care Products L.P. Product Data for Cosmocil® CQ.*
Australian Patent Office's Examiner's Report dated Mar. 4, 2010 for Australian application No. 2007317907.
Taiwanese Office Action dated Feb. 10, 2012 for Taiwanese patent app. No. 098120683.
Chinese Office Action dated Feb. 22, 2012 for Chinese patent app. No. 200780041027X.
Olsen et al. Abstract: "Increase in tear film lipid layer thickness following treatment with warm compresses in patients with meibomian gland dysfunction." Apr. 2003 http://www.ncbi.nlm.nih.gov/entrez/query.fcgi?cmd=Retrieve&db=PubMed&list_uids=12695712&dopt=Abstract.
Greiner J.V. et al.: "Effects of Eyelid Scrubbing on the Lid Margin" The CLAO Journal, vol. 25, No. 2, Apr. 1999, pp. 109-113 http://journals.lww.com/claojournal/Abstract/1999/04000/Effects_of_Eyelid_Scrubbing_on_the_Lid_Margin.10.aspx.
"Blepharitis" The Eye Digest May 5, 2003, pp. 1-4. www.agingeye.net/otheragingeye/blepharitis.php.
Hannsmann F. et al: Polyhexamethylenbiguianid (PHMB) aur praoperativen Antisepsis bei Kataraktoperation: Der Opthalmologe, vol. 4 Apr. 2004, pp. 377-383 (Polyhexamethlybiguanid as a preoperative antiseptic for cataract surgery). http://www.ncbi.nlm.nih.gov/pubmed/15067419.
Key J.M., "A Comparative Study of Eyelid Cleaning Regimens in Chronic Blepharitis" The CLAO Journal, vol. 22, No. 3, Jul. 1996, pp. 2009-212, Dept. of Ophthalmology, Baylor College of Medicine, Houston, TX, USA.
"OCuSOFT Lid Scrub" Apr. 26, 2005. http://www.ocusoftlidscrub.com/.
Polack F.M. et al., Liebowitz H.M. et al.: "Experience with a new detergent lid scrub in the management of chronic blepharitis" Arch Opthalml, vol. 106, No. 6, Jun. 1988, pp. 719-20. http://archopht.jamanetwork.com/article.aspx?articleid=637270#References.
International Search Report and Written Opinion dated Mar. 2, 2015 for co-pending PCT patent app. No. PCT/US14/45738.

* cited by examiner

OCULAR COMPOSITION AND KITS THEREOF

FIELD OF THE INVENTION

Compositions, methods, and kits useful for cleansing the eyelids and maintaining eyelid hygiene are disclosed.

BACKGROUND OF THE INVENTION

Blepharitis is a common chronic inflammation of the eyelids characterized by a scaly crust on the lid margins. It can be caused by a bacterial infection, or it can be allergic in origin or associated with seborrhea of the face and scalp. Blepharitis can be treated and prevented by cleansing the eyelids on a regular basis and maintaining proper ocular hygiene.

Often associated with or secondary to blepharitis is a bacterial infection of the surface of the skin at the edge of the lid known as an external hordeolum or of the meibomian glands, either, commonly referred to as sties. Such conditions also are accompanied by pain, redness and tenderness of the lid margins. Although sties are often recurring, such conditions can be minimized by regular cleansing of the eyelid margins.

Glands in and around the lid margins secrete oil which in some individuals can build up in the eyelashes and on the lids. This build up of oil is usually accompanied with cellular debris, dust and the like. Obviously, if this build up is excessive, the likelihood of a bacterial infection will be increased.

Historically, blepharitis conditions have been treated by using "homemade" solutions of dilute baby shampoo. This required the patient to dilute the baby shampoo with tap water and then use the dilute solution with a cotton-tipped applicator pad or the like to cleanse the eyelids. Often simple skin cleansers are unsuited for use on the eyelid. Eyelid cleansers must be non-irritating to both the sensitive skin around the eye and the eye tissue itself, while having an antimicrobial effect.

SUMMARY OF THE INVENTION

The composition of the present invention is effective as an eye cleanser. The composition consists essentially of purified water, PEG-80 sorbitan laurate, sodium trideceth sulfate, PEG-150 distearate, sodium lauroamphoacetate, cocamidopropyl hydroxysultaine, sodium laureth-13 carboxylate, sodium chloride, PEG-15 cocopolyamine, polyhexamethylene biguanide, potassium sorbate, 1,2 hexanediol, and caprylyl glycol. The use of non-irritating ingredients that also exhibit antimicrobial benefits in the ocular composition increases its cleansing ability. The present invention offers convenient combination therapy for improving overall eyelid hygiene and also providing for adjunctive eyelid therapy.

In one embodiment, the ocular composition is suitable for daily eyelid hygiene therapy. The ocular composition can be formulated as an emulsion, a suspension, a dispersion, a foam, a cream, a lotion, a solution, a paste, a gel or a spray.

In one embodiment, a kit comprising an ocular composition consisting essentially of PEG-80 sorbitan laurate, sodium trideceth sulfate, PEG-150 distearate, sodium lauroamphoacetate, cocamidopropyl hydroxysultaine, sodium laureth-13 carboxylate, sodium chloride, PEG-15 cocopolyamine, polyhexamethylene biguanide, potassium sorbate, 1,2 hexanediol, and caprylyl glycol is provided. The various embodiments of the kit of the invention facilitate both treatment of infected eyelids and proper cleansing of the eyelids to prevent recurring infections. The kit comprises one or more containers comprising the ocular composition in solution form. The kit further comprises one or more applicators for applying the solution. The applicators comprise eyelid pads, disposable swabs or cotton balls.

In another embodiment, the kit comprises a suitable pump dispenser. The pump dispenser can include the ocular composition and can be used for dispensing as foam the ocular composition. In another embodiment, the kit includes a container for the ocular composition.

In yet another embodiment, the kit comprises one or more pads pre-moistened with the ocular composition. The pre-moistened pads may be conveniently applied to eyelids to be treated or cleansed and discarded after use. The pre-moistened pads may be individually sealed and enclosed within impervious containers or wrappers.

The ocular composition may be applied to the eyelid by applying an effective amount of the composition to the eyelid. Optionally, the ocular composition may be rubbed onto the eyelid to induce foaming.

DETAILED DESCRIPTION

The composition of the invention is effective as an eyelid cleanser, or scrub, as it has an antimicrobial effect, but is still practically non-irritating to the eye. The composition has these beneficial characteristics because of the combination of polyhexamethylene biguanide (PHMB) and Symdiol. Symdiol is a combination of 1,2-hexanediol and 1,2-octanediol. The PHMB-Symdiol combination has a synergistic anti-microbial effect. In addition, the composition of this invention avoids traditional pH adjusters by using a pH stabilizing surfactant solution. Elimination of traditional pH adjusters reduces the amount of irritation caused by the composition in comparison to prior eyelid cleansers.

One embodiment of the ocular composition is suitable for daily eyelid hygiene therapy and consists essentially of water, PEG-80 sorbitan laurate, sodium trideceth sulfate, PEG-150 distearate, sodium lauroamphoacetate, cocamidopropyl hydroxysultaine, sodium laureth-13 carboxylate, sodium chloride, PEG-15 cocopolyamine, polyhexamethylene biguanide, potassium sorbate, 1,2 hexanediol, and caprylyl glycol.

For the purposes of this invention, polyhexamethylene biguanide (PHMB) is pseudonymous for polyhexamethylene biguanide, polyhexamethylene biguanide hydrochloride, and polyaminopropyl biguanide. 1,2-octanediol is also known as caprylyl glycol. Combining PHMB with 1,2-hexanediol and 1,2-octanediol has a synergistic antimicrobial effect.

To avoid the irritating effects of traditional pH adjusters, the pH stabilizing surfactant solution is prepared to provide a pH stabilized composition. Surfactants also increase cleansing ability of the composition and have a foaming capability. PHMB is most effective as an antimicrobial agent in pH ranges between 5.5 and 7.5. Therefore, it is desirable to control the pH level of the composition within this range by use of a blend of surfactants. It is also desirable that the ocular of the present invention has a foaming ability to facilitate physical cleansing of the eyelid. Consequently, surfactants must be chosen which will both control the pH of the composition within PHMB's effective range and provide the foaming ability necessary to physically clean the eyelid.

Advantageously, controlling the pH of the composition with a surfactant solution rather than traditional pH adjusters has safety benefits as many traditional pH adjusters are irritating to the eye. In general, surfactants are less irritating to the eye than traditional pH adjusters. Examples of traditional pH adjusters, include basic pH adjusters, such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine), and acidic pH adjusters, such as mineral acids and polycarboxylic acids (e.g., hydrochloric acid, nitric acid, phosphoric acid, sulfuric acid, citric acid, glycolic acid, and lactic acid).

In an embodiment of this invention a microbiological preservative is included. The preservative preferred is potassium sorbate, polyamino propyl biguanide or caprylyl glycol.

In addition to reduced irritation, many surfactants have the added capability of producing a foam which assists in the cleansing ability of the composition. To form the pH stabilizing surfactant solution, one or more foam producing surfactants are first chosen to provide the foaming ability of the composition. Suitable surfactants include anionic, nonionic, and amphoteric surfactants.

To determine the correct amount of each surfactant to include in the ocular composition, the pH of the entire composition, the foaming capacity of composition, and the cleansing ability of the composition are tested. The pH level of the composition is measured with a pH meter and the amount of the individual surfactants adjusted to control the composition's pH within the desired pH range.

The composition's foaming capability is measured according to the Ross Miles method. This measurement involves producing foam from the composition and measuring the height and stability of the foam over time. The foam is created by pouring the composition from a set height into itself for five minutes. Alternatively, where the composition has a low foam capability, the composition is agitated with a turbine agitator for a set time to produce the foam. The thickness of the foam is measured at timed intervals. To achieve the desired foaming capability, the amounts of foam producing surfactants in the composition are varied.

The cleansing capabilities of the composition are tested by anecdotal human testing. Humans apply the composition to the eyelid and cleanse the eyelid. The humans report the levels of irritation, skin tightness and overall feeling of cleanness caused by the composition. The amounts and types of surfactants employed are adjusted in response to the reports.

Through the adjustment of the amounts and types of surfactants used in the pH stabilizing surfactant solution in response to test results of the pH level, foaming capacity, and cleansing capabilities, an effective amount of pH stabilizing surfactant composition to be used is determined. The combination of the pH stabilizing surfactant solution with PHMB, 1,2-hexanediol and 1,2-octanediol forms the composition of this invention.

In a first embodiment, the composition of this invention comprises PHMB, 1,2-hexanediol, and 1,2-octanediol in combination with a pH stabilizing surfactant solution. Suitable surfactants to be used in the pH stabilizing surfactant solution include amphoteric surfactants, anionic surfactants, and nonionic surfactants.

In one embodiment, the pH stabilizing surfactant solution comprises sodium lauroamphoacetate, polyoxyethylene 80 sorbitan monolaurate, decyl polyglucoside, and a modified Ringer's solution. Sodium lauromaphoacetate is an amphoteric surfactant. Polyoxyethylene 80 sorbitan monolaurate and decyl polyglucoside are both nonionic surfactants.

In still another embodiment, the composition of this invention can further include one or more moisturizers. Moisturizers are chemicals that prevent transepidermal water loss. Moisturizers may prevent water loss by forming a film over the skin to prevent water from evaporating from the skin. Alternatively, moisturizers comprise hydroscopic molecules that draw water from the air into the skin.

In a further embodiment, the composition also comprises a foam stabilizer. A foam stabilizer is a chemical which increases the lifetime of the foam. The foam stabilizer can be a polyethylene glycol diester of methyl glucose and a fatty acid. Suitable fatty acids include oleic acid, steric acid, lauric acid, caprylic acid, and capric acid. Suitably, the foam stabilizer is PEG-150 distearate.

One specific embodiment of the composition consists of polyhexamethylene biguanide, 1,2-hexanediol,1,2-octanediol, D-panthenol, sodium lauroamphoacetate, polyoxyethylene-80 sorbitan monolaurate, decyl polyglucoside, methyl gluceth-20, and PEG-120 methyl glucose dioleate.

In one embodiment, a eyelid treatment kit suitable for both adjunctive eyelid therapy and hygiene maintenance is provided. The eyelid treatment kit further comprises the ocular composition described earlier. The ocular composition can be used for removing oil, debris and desquamated skin which may cause eye irritation. The ocular composition also may offer a wide range of anti-bacterial properties for treating moderate to severe eyelid conditions.

The ocular composition can be in a form chosen from an emulsion, a suspension, a dispersion, a foam, a cream, a lotion, a solution, a paste, a gel or a spray. In one embodiment, the eyelid treatment kit can include a pump dispenser for dispensing the ocular composition. The pump dispenser dispenses an instant foam liquid that generates pre-lathered foam immediately upon depressing its control-tip pump. This is an instant foam formula for routine eyelid hygiene or ongoing eyelid-maintenance. For convenience and economy, the size of the pump dispense can range from about 2 oz. bottle to a 16 oz. bottle. A user can pump a desired amount of the ocular composition foam onto a clean, lint-free washcloth, or on the fingertips and gently cleanse the lids using lateral side to side strokes after which the eyelids are rinsed thoroughly. The foaming ocular composition provides patients who are on a lid-hygiene regiment with added convenience.

In another embodiment, the eyelid treatment kit may include a container comprising the ocular composition. The container may be selected from a glass bottle, a plastic bottle, or other suitable material known in the art. For convenience and economy, the bottles may range in size from about 30 ml to 480 ml. The kit may further comprise one or more applicators for applying ocular composition in the container. The applicator may be selected from a group consisting of a swab, a fabric pad, or cotton balls. The composition may be applied to the eye by loading the applicator with a desired amount of ocular composition and cleansing the eyelid using lateral side to side strokes. In another aspect of the invention, paper towels, cotton balls or even the fingertips can by employed to apply the ocular composition.

The eyelid treatment kit can further include one or more eyelid pads pre-moistened with the ocular composition. The pre-moistened eyelid pads are dimensioned to receive an amount ranging from about 1.0 gram to about 2.0 grams of the ocular composition. In one aspect, the pre-moistened eyelid pad comprises a lint-free non-abrasive rayon and polypropylene fabric blend. In another aspect, the fabric pad comprises a textured surface to absorb and retain the ocular composition. However, the fabric pad must remain soft enough so as to not be harsh on the user's skin. Preferably, the fabric pads further comprise a moisturizer blend that is non-drying and non-irritating.

The fabric pad must be selected so that the fabric is capable of containing the ocular composition in the interstitial spaces of the fabric's weave. In one aspect, the fabric pad comprises two sheets of fabric, a first sheet of fabric and a second sheet of fabric. The two pieces may be held together by stitching them together on the sides. The fabric pad can have a surface area dimensioned to receive an effective amount of the ocular composition.

The pre-moistened fabric pad may also be sealed in a sealable container that encloses the pre-moistened fabric pad. In one aspect, the sealable container may comprise a box, or a tub, or a package. The sealable container may be made of any suitable material including plastic or a metal foil material. The pre-moistened fabric pads may be individually packages for use. In one aspect, the sealable container may be an impervious wrapper so that the fabric pad with the ocular composition does not come into contact with contaminants and remains moistened for a long period of time. The pre-moistened fabric pads are applied or scrubbed using lateral side to side strokes on to the eyelids and other periocular regions that need to be cleansed or treated. The eyelids are rinsed with water and the used fabric pads are discarded.

In another embodiment, instructions for use of the various components of the eyelid treatment are included within the kit. The instructions can be printed in a manual included within the kit on instruction sheets or they may be printed directly on the housing. If the instructions are printing on the housing, they may be printed on the outside of the housing or on the inside of the housing where the instructions are not visible to the user of the eyelid treatment kit until the user opens the kit. As an alternative, the instructions may be printed on the containers or packaging of the individual components of the eyelid treatment kit.

The components of the kit may be enclosed in suitable housing. The housing may be any type of container or means for securing the components of the eyelid treatment kit. A preferred embodiment of the housing may be a size such that the components of the kit are secured snugly within the housing thereby preventing unnecessary movement or shifting of the various components. The housing and the components within the housing may also be sized for the purposes of economy and/or convenience.

The composition of the present invention may be used to cleanse an eyelid. To cleanse the eyelid, an effective amount of the ocular composition can be applied to the eyelid. The ocular composition may be rubbed on the eyelid to induce foaming, which facilitates cleansing of the eyelid. In another aspect of the method of using the composition of this invention, the ocular composition is applied to the eyelid from a fabric pad. The ocular composition may be rubbed on the eyelid with a fabric pad to induce foaming, which assists in the cleansing ability of the eyelid scrub.

It has been discovered that ocular composition, according to the one or more embodiments, described earlier is phase stable, freeze-thaw stable and non-irritating. It can then be used by patients without dilution, further mixing or the like so that there will be a high patient acceptance of the composition. Use on a regular basis then will prevent the build-up of oil, dust or the like which can harbor bacteria in the eyelids which in turn can cause irritation, blepharitis, sties, and the like. The ocular composition, in accordance with an embodiment, is clear, has a viscosity similar to water and a specific gravity of 0.987.

While the invention has been described with reference to various embodiments, the invention is not limited to the specific examples given, and other embodiments and modifications can be made by those skilled in the art without departing from the spirit and scope of the invention. Also, the composition is described as useful as an eyelid cleanser. It should be readily understood that the composition of this invention may be used for other applications.

Furthermore, while compositions, kits and methods are described in terms of "comprising," "containing," or "including" various components or steps, the compositions, kits and methods also may "consist essentially of" or "consist of" the carious components and steps. Any numerical range with a lower limit and upper limit disclosed also specifically discloses any number and any included range falling within said range. The terms in the claims have their plain, ordinary meaning unless otherwise and clearly defined by the patentee. The indefinite articles "a" or "an", as used in the specification and claims, are defined herein to mean one or more than one of the element that it introduces. If there exists any conflict in the usages of a word or term in this specification and one or more patents or other documents that may be incorporated herein by reference, the definitions that are consistent with this specification should be adopted.

The invention claimed is:

1. An ocular composition consisting of:
purified water;
PEG-80 sorbitan laurate;
sodium trideceth sulfate;
PEG-150 distearate;
sodium lauroamphoacetate;
cocamidopropyl hydroxysultaine;
sodium laureth-13 carboxylate;
sodium chloride;
PEG-15 cocopolyamine;
polyhexamethylene biguanide;
potassium sorbate;
1,2 hexanediol; and
Caprylyl glycol.

2. An eyelid treatment kit, wherein the kit comprises an ocular composition,
wherein the ocular composition consists essentially of water, PEG-80 sorbitan laurate, sodium trideceth sulfate, PEG-150 distearate, sodium lauroamphoacetate, cocamidopropyl hydroxysultaine, sodium laureth-13 carboxylate, sodium chloride, PEG-15 cocopolyamine, polyhexamethylene biguanide, potassium sorbate, 1,2 hexanediol, and caprylyl glycol.

3. The eyelid treatment kit of claim 2, wherein the ocular composition is in a form chosen from an emulsion, a suspension, a dispersion, a foam, a cream, a lotion, a solution, a paste, a gel or a spray.

4. The eyelid treatment kit of claim 2, further comprising a pump dispenser, wherein the pump dispenser contains the ocular composition.

5. The eyelid treatment kit of claim 4, wherein the ocular composition is capable of forming a foam when dispensed from the pump dispenser.

6. The eyelid treatment kit of claim 3, further comprising a container for the ocular composition.

7. The eyelid treatment kit of claim 6, further comprising one or more applicators for applying the ocular composition.

8. The eyelid treatment kit of claim 7, wherein the applicator is selected from a group consisting of a swab, a fabric pad and cotton balls.

9. The eyelid treatment kit of claim 8, wherein the applicator is a fabric pad.

10. The eyelid treatment kit of claim 8, wherein a fabric pad is pre-moistened with the ocular composition.

11. The eyelid treatment kit of claim 8, wherein the fabric pad comprises a textured surface.

12. The eyelid treatment kit of claim 8, wherein the fabric pad comprises a rayon and polypropylene fabric blend.

13. The eyelid treatment kit of claim 8, wherein the fabric pad comprises about 30 ml to about 480 ml of the ocular composition.

14. The eyelid treatment kit of claim 9, further comprising a sealable container enclosing the fabric pad.

15. The eyelid treatment kit of claim 9, further comprising an impervious wrapper for enclosing the fabric pads.

16. A method of cleansing an eyelid with an ocular composition comprising:
   applying an effective amount of the ocular composition of claim 1 to the eyelid.

17. The method of claim 16, wherein the ocular composition is applied to the eyelid from a fabric pad.

18. The method of claim 17, wherein the fabric pad comprises about 30 ml to about 480 ml of the ocular composition.

19. The method of claim 17, wherein the ocular composition induces foaming.

\* \* \* \* \*